United States Patent
Thiele

(10) Patent No.: US 9,028,802 B2
(45) Date of Patent: May 12, 2015

(54) METHOD OF DIFFERENTIALLY DIAGNOSING DIFFERENT TYPES OF DEMENTIA

(71) Applicant: Koninklijke Philips Electronics N.V., Eindhoven (NL)

(72) Inventor: Frank Olaf Thiele, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/683,022

(22) Filed: Nov. 21, 2012

(65) Prior Publication Data

US 2013/0084244 A1 Apr. 4, 2013

Related U.S. Application Data

(62) Division of application No. 12/679,317, filed as application No. PCT/IB2008/053853 on Sep. 23, 2008, now abandoned.

(30) Foreign Application Priority Data

Sep. 26, 2007 (EP) .................................. 07117262

(51) Int. Cl.
    *A61K 49/04* (2006.01)
    *A61K 51/04* (2006.01)
(52) U.S. Cl.
    CPC ......... *A61K 51/0455* (2013.01); *A61K 51/0448* (2013.01)
(58) Field of Classification Search
    CPC ... A61K 49/00; A61K 49/001; A61K 49/004; A61K 49/0002; A61K 49/0017; A61K 49/0433; A61K 19/0438; A61K 49/0442; A61K 51/00; A61K 51/04; A61K 51/0406; A61K 51/0491; A61K 51/08; A61K 51/088; A61K 51/0455; A61K 51/0448; C07D 451/02
    USPC ........... 424/1.11, 1.45, 1.65, 1.81, 1.85, 1.89, 424/9.1, 9.4, 9.42, 9.43, 9.44, 9.45; 546/124, 132; 534/7, 10–16
    See application file for complete search history.

(56) References Cited

U.S. PATENT DOCUMENTS

| 5,493,026 | A | * | 2/1996 | Elmaleh et al. ............... 546/132 |
| 5,980,860 | A | | 11/1999 | Kung |
| 6,180,083 | B1 | * | 1/2001 | Mauclaire et al. ........... 424/1.85 |
| 2002/0150535 | A1 | | 10/2002 | Madras |

FOREIGN PATENT DOCUMENTS

WO 2009058851 A2 5/2009

OTHER PUBLICATIONS

Chiu et al (J. Formos Med. Assoc. 2006, vol. 105, No. 7, pp. 556-562).*
Alzheimer's Association (http://www.alz.org/dementia/types-of-dementia.asp, online publication date unknown, 10 pages).*
Koeppe et al "11C-DTBZ and 18F-FDG PET Measures in Differentiating Dementias", The Journal of Nuclear Medicine, vol. 46, No. 6. Jun. 2005, pp. 936-944.
Jagust, "Molecular Neuroimaging in Alzheimer's Disease", NeuroRx: The Journal of the American Society for Experimental Neurotherapeutics, vol. 1, Apr. 2004, pp. 206-212.
Matsuda, "Role of Neuroimaging in Alzheimer's Disease, With Emphasis on Brain Perfusion Spect", Alzheimers Disease and Spect, vol. 48, 2007, pp. 1289-1300.
Walker, Z. et al: "Differentiation of Demential with Lewy Bodies from Alzheimer's Disease using a Dopaminergiv Presynaptic Ligant", Journal of Neurology Neurosurgery and Physiatry, vol. 73, No. 2, 2002, pp. 134-140.
Donnemiller, E. et al; "Brain Perfusion Scintigraphy with <99m>Tc-HMPAO or >99m>Tc-ECD and <123>I-[beta]-CIT Single PHoton Emission Tomography in Dementia of the Alzheimer-type and diffuse Lewy Body Disease" Eupopean Journal of Nuclear Medicine 1997, vol. 24, No. 3, pp. 320-325.
Madras, Bertha K. et al "ALtropane, a SPECT or PET Imaging Prove for Dopamine Neurons: I. Dopamine Transporter Binding in Primate Brain", Synapse, vol. 29, No. 2, Jun. 1998, pp. 93-104.
Khoshbouei, Habibeh et al "N-Terminal Phosphorylation of the DOpamine Transporter is Required for Amphetamine-Induced Efflux", PLOS Biology, Mar. 2004, vol. 2, No. 3, pp. 0387-0393.
Mito, Yasunori et al, Brain 3D-SSP SPECT Analysis in Dementia with Lewy Bodies, Parkinson's Disease with and without Dementia, and Alzheimer's Disease, Clinical Neurology and Neurosurgery, vol. 107, 2005, pp. 396-403.
Marshall, Vicky et al "Role of Dopamine Transporter Imaging in Routine Clinical Practice" Movement Disorders, vol. 18, No. 12, 2003, pp. 1415-1423.
Sedaghat, Fereshteh et al "Evaluation of Dopaminergic Function in Frontotemporal Demential using 123 I-FP-CIT Single Photon Emission Computed Tomography" Neuro-Degenerative Diseases, vol. 4, No. 5, Jul. 2007, pp. 382-385.
Lehericy, Stephane et al "Neuro-Imagerie des Demences" Presse Medicale, 2007, vol. 36, No. 10 11, pp. 1453-1463.
Walker, Z. et al "Differentiation of Dementia With Lewy Bodies From Alzheimer's Disease Using a Dopaminergic Presynaptic Ligand" Journal Neurol Neurosurgery Psychiatry, 2002, vol. 73, pp. 134-140.

* cited by examiner

*Primary Examiner* — D L Jones

(57) ABSTRACT

The present invention relates to a method of differentially diagnosing different types of dementia. In particular, the method relates to the use of specific SPECT tracers for differentially diagnosing Alzheimer's disease, Lewy-Body Dementia, and Frontotemporal Dementia.

4 Claims, No Drawings

METHOD OF DIFFERENTIALLY DIAGNOSING DIFFERENT TYPES OF DEMENTIA

CROSS REFERENCE TO PRIOR APPLICATIONS

The present application is a divisional of U.S. application Ser. No. 12/679,317, filed on Mar. 22, 2010, which is the U.S. National Stage application of International Application No. PCT/IB2008/053853 filed on Sep. 23, 2008, which claims priority to EP 07117262.1 filed on Sep. 26, 2007. These applications are incorporated by reference herein in their entireties.

SUBJECT OF THE INVENTION

The present invention relates to the field of diagnosing different types of dementia.

BACKGROUND OF THE INVENTION

Dementia is a highly prevalent problem causing considerable disability and even mortality. Among the most common forms of dementia are the three degenerative forms Alzheimer's disease (AD), dementia with Lewy bodies (also known as Lewy-Body Dementia (DLB)), and Frontotemporal Dementia (FTD).

Various lines of research, including clinical, pathological, and genetic analysis indicate that the degenerative forms of dementia have different underlying etiologies and pathogenetic mechanisms.

Given the presumably different mechanisms underlying the aforementioned types of dementia, future therapies will probably differ for each major form of degenerative dementia. The ability to differentially diagnose between Alzheimer's disease, Lewy-Body Dementia, and Frontotemporal Dementia will be a major advantage not only for the individual patient being treated, but also with respect to the economic strains of public health systems. However, at present, precise differentiation of Alzheimer's disease, Lewy-Body Dementia, and Frontotemporal Dementia is only possible by post-mortem analysis of brain tissue.

Despite the lack of specific therapeutic regimens for the aforementioned different types of degenerative dementia, pre-mortem diagnosis is already an issue today, as an accurate diagnosis will have clinical utility. For example, precise diagnosis is important when counseling patients and families about prognosis and the question of whether e.g. cholinesterase inhibitor therapy should be undertaken, given that it is not considered to be effective for Frontotemporal Dementia. Patients suffering from Lewy-body Dementia are susceptible to neuroleptic agents.

At present, positron emission tomography (PET) and single photon emission computer tomography (SPECT) are used to undertake pre-mortem analysis of patients suspected of suffering from dementia.

In the past, FDG-PET and perfusion SPECT have been shown to discriminate patients suffering from Alzheimer's disease from normal controls, while allowing some degree of differential diagnosis between Alzheimer's disease and Frontotemporal Dementia (see Jagust et al. (2004), Neuro Rx, 1: 206-212, Matsuda (2007), J Nucl Med 48:1289-1300). However, differential diagnosis of Alzheimer's disease versus Lewy-Body Dementia currently requires an additional SPECT analysis, meaning that a differential diagnosis for Alzheimer's disease, Lewy-body Dementia, and Frontotemporal Dementia currently requires different PET and SPECT sessions.

Thus there is a continuing need for efficient methods that allow for differential diagnosis of degenerative types of dementia.

OBJECT AND SUMMARY OF THE INVENTION

It is one objective of the present invention to provide diagnostic compositions which can be used for differential diagnosis of different types of dementia.

It is a further objective of the present invention to provide methods of diagnosing differentially between different types of dementia.

Yet another objective of the present invention relates to methods of data acquisition, the data of which may be used later on for differential diagnosis of different types of dementia.

These and other objectives, as they will become apparent in the ensuing description, are attained by the subject matter of the independent claims. Some of the preferred embodiments are reflected in the dependent claims.

The present invention is based on the finding that SPECT tracers of distinct properties can be used for the differential diagnosis of Alzheimer's disease, Lewy-Body dementia, and/or Frontotemporal Dementia.

The present invention, in one of its embodiments, thus relates to a diagnostic composition for the differential diagnosis of Alzheimer's disease, Lewy-Body Dementia and/or Frontotemporal Dementia comprising at least one compound which is suitable for single photon emission computer tomography (SPECT), which is capable of crossing the blood brain barrier and which can associate with a Dopamine Transporter (DAT).

Such compounds, which in the context of the present invention may also be designated as SPECT tracers, will in some of their embodiments be labeled with $^{99m}$Tc and/or $^{123}$I.

SPECT tracers which are suitable for the differential diagnosis of Alzheimer's disease, Lewy-Body Dementia, and Frontotemporal Dementia may typically comprise the following structural element:

Preferred embodiments of compounds that may be used for the diagnostic composition of the present invention are Technepin, Fluoratec, Trotec-1, Trodat-1, Altropane, Dopascan, and Datscan. The molecular structures of these compounds will be depicted hereinafter.

The present invention also relates to the use of the aforementioned compounds in the manufacture of a diagnostic composition for the differential diagnosis of Alzheimer's disease, Lewy-Body Dementia, and/or Frontotemporal Dementia. The present invention further relates to a method of data acquisition comprising at least the following steps:

administering at least one compound which is suitable for SPECT, which is capable of crossing the blood brain barrier and which can associate with a Dopamine Transporter (DAT) to a human or animal being;

measuring said compound's distribution within the brain using SPECT at a time point $x_1$; and measuring said compound's association with DAT within the brain at a time point $x_2$, wherein $x_2$ is later than $x_1$.

In one embodiment, the method of data acquisition will be performed using compounds as described above for the diagnostic compositions. Thus, the compounds will be typically labeled with $^{99m}$Tc and/or $^{123}$I.

In a preferred embodiment, the method will rely on compounds which comprise the following structural elements:

In yet another preferred embodiment, the method will rely on compounds being selected from the group comprising Technepin, Fluoratec, Trotec-1, Trodat-1, Altropane, Dopascan, and/or Datscan.

Yet another embodiment of the present invention relates to a method of diagnosis comprising at least the following steps:
administering at least one compound which is suitable for SPECT, which is capable of crossing the blood brain barrier and which can associate with a Dopamine Transporter (DAT) to a human or animal being;
measuring said compound's distribution within the brain using SPECT at a time point $x_1$; and
measuring said compound's association with DAT within the brain at a time point $x_2$, wherein $x_2$ is later than $x_1$
comparing the obtained results with an appropriate control;
deciding on the occurrence of Alzheimer's disease, Lewy-Body Dementia, and Frontotemporal Dementia.
As for the manufacture of the afore-mentioned diagnostic composition or the method of data acquisition, the method of diagnosis may be performed using the above-described compounds. Compounds which have been mentioned above as being particularly suitable for use in the diagnostic compositions or for performing the method of data acquisition approach will also be considered to be useful for the method of diagnosis aspect of the invention.

DETAILED DESCRIPTION OF THE INVENTION

The inventor has surprisingly discovered that SPECT tracers can be used for differentially diagnosing degenerative dementias such as Alzheimer's disease, Lewy-Body Dementia, and Frontotemporal Dementia in a single SPECT run. The invention is based on the finding that SPECT tracer distribution as measurable by perfusion analysis shortly after administration of the tracer and the SPECT tracer's localization as measurable after a longer period can be used to differentially diagnose the aforementioned degenerative dementia.

Before some of the embodiments of the present invention are described in more detail, the following definitions are introduced.

As used in the specification and in the claims, the singular forms of "a" and "an" also include the respective plurals unless the context clearly dictates otherwise.

The terms "about" and "approximately" in the context of the present invention generally denote a level or interval accuracy that a person skilled in the art will understand to still ensure the technical effect of the feature in question. As regards numerical values, these terms typically indicate a deviation from the indicated numerical value of ±10% and preferably of ±5%.

It is to be understood that the term "comprising" is not limiting. For the purposes of the present invention, the term "consisting of" is considered to be a preferred embodiment of the term "comprising of". If hereinafter a group is defined to comprise at least a certain number of embodiments, this is also meant to disclose a group which preferably consists only of these embodiments.

Further definitions of terms will be given in the context of which the terms are used.

As mentioned above, the present invention is based on the finding that differential diagnosis of Alzheimer's disease, Lewy-Body Dementia, and Frontotemporal Dementia may be achieved by administering a SPECT tracer compound to a human or animal being, wherein the compound is capable of being detected by SPECT, is capable of crossing the blood brain barrier, and is capable of associating with the Dopamine Transporter (DAT), and then performing a SPECT analysis.

In accordance with the invention, SPECT images of perfusion of the compound shortly after administration to the human or animal subjects are recorded and further SPECT images are recorded later on when the compound has associated in those areas of the brain in which Dopamine Transporters (DAT) are localized, such as the nigrostriatum. The resulting pictures may then be used as will be explained hereinafter to differentially diagnose Alzheimer's disease, Lewy-Body Dementia, and Frontotemporal Dementia.

For the purposes of the present invention, the term "SPECT tracer" refers to a compound which is capable of being detected by SPECT analysis.

Further, for the purposes of the present invention, the terms "Alzheimer's disease," "Lewy-Body Dementia," and "Frontotemporal Dementia" have the meaning by which they are commonly used in the art.

The term "perfusion" relates to the distribution of a compound within the brain as measurable by a SPECT analysis. For the purposes of the present invention, perfusion is indicative of, even though it is not identical to, metabolic activity within the brain. Thus, if a SPECT analysis shows a rather high perfusion, i.e. a high presence in a certain area of the brain, it is considered to be indicative of a high, i.e. hypermetabolic activity within that area of the brain. If, on the other hand, a SPECT analysis reveals that the respective SPECT is found at a low perfusion rate, i.e. at a low amount in a certain area within the brain, it is considered to be indicative of a low or even a hypometabolic activity.

The phrase "association with a Dopamine Transporter" in this context means that a SPECT tracer interacts either directly or indirectly with a Dopamine Transporter and thus localizes in an area within the brain where Dopamine Transporters are characteristically found. The term "association with a Dopamine Transporter" may, therefore, refer to a situation where the SPECT tracer directly acts, e.g. functions as a ligand on the Dopamine Transporter. However, the term may also refer to a situation where the SPECT tracer is found to localize to the same or comparable areas as dopamine receptors by interacting with e.g. cellular factors such as proteins that also bind to the dopamine receptors.

The term "associated with Dopamine Transporter" may preferably designate the SPECT tracer's ability to localize within the nigrostriatum.

As mentioned, one embodiment of the present invention relates to a diagnostic composition for the differential diagnosis of Alzheimer's disease, Lewy-Body Dementia and/or Frontotemporal Dementia comprising at least one compound which is suitable for single photon emission computer tomography (SPECT), which is capable of crossing the blood brain barrier and which can associate with a Dopamine Transporter (DAT).

A person skilled in the art is well aware that compounds which are suitable for SPECT detection must be labeled with a radionuclide. Such radionuclides are typically $^{99m}$Tc and/or $^{123}$I.

It is emphasized that the compounds which may be used in the diagnostic compositions of the present invention do not need to have a certain structural element, but are required to adapt a structure which allows them to cross the blood brain barrier and to associate with a Dopamine Transporter. Of course, these capabilities must be observed for the compounds to be used in the diagnostic compositions of the present invention when the compounds further comprise a radionuclide such as $^{99m}$Tc and/or $^{123}$I that renders them suitable for SPECT analysis.

In certain embodiments of the present invention, the SPECT compound, in addition to radionuclides such as $^{99m}$Tc or $^{123}$I, may comprise the following structural element:

In preferred embodiments of the present invention, the compound may comprise the following structures as depicted in Table 1:

A particular preferred compound is Altropane.

Other tracer molecules that may be used can be found inter alia in U.S. Pat. No. 5,980,860, US 2002/0150535, and U.S. Pat. No. 5,493,026.

As mentioned above, the SPECT tracers may preferably display their capacity to associate with a dopamine receptor

TABLE 1

Technepine

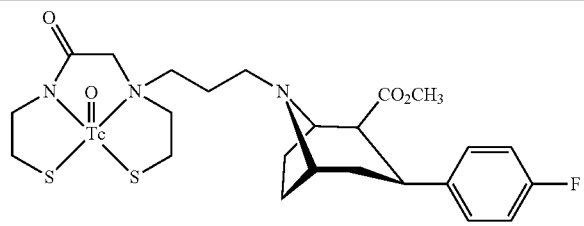

Fluoratec (O-1505T)

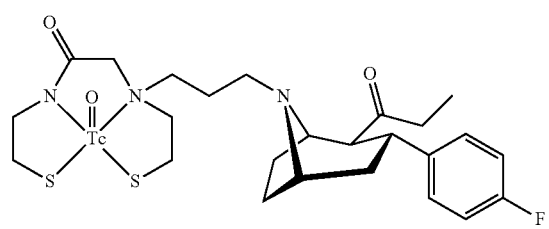

TROTEC-1

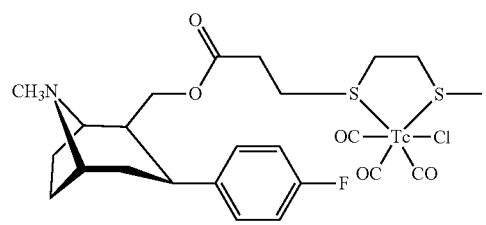

TRODAT-1

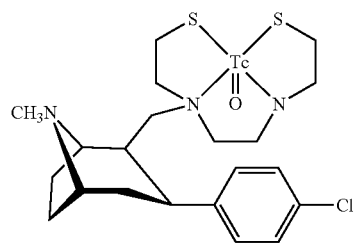

Altropane

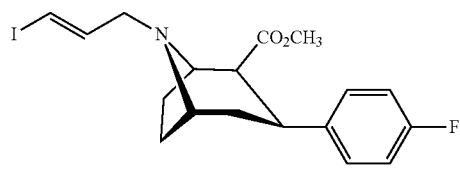

Dopascan (RTI-55 or β-CIT)

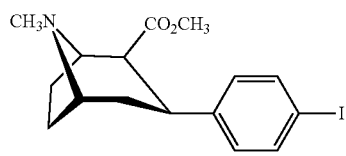

DaTSCAN (FP-CIT)

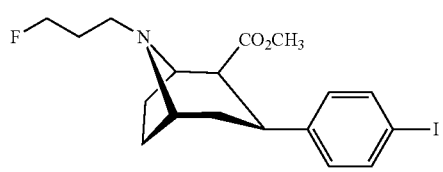

by localizing to the nigrostriatum. In a preferred embodiment, SPECT tracers such as those depicted in Table 1 are used that have the capability of binding to nigrostriatal terminals and allowing the determination of nigrostriatal integrity.

The diagnostic compositions for the differential diagnosis of Alzheimer's disease, Lewy-Body Dementia, and Frontotemporal Dementia may comprise additional excipients besides the compounds that are used for the SPECT analysis. Such additional excipients will typically be pharmaceutically acceptable and may include e.g. buffers, diluants, fillers, lubricants, etc. These optional pharmaceutically acceptable excipients will be selected depending on how the diagnostic composition is formulated. A person skilled in the art is aware that a diagnostic composition that is to be injected may use different excipients than e.g. a diagnostic composition that is to be applied orally, rectally, or via subcutaneous injection. It is well within a skilled person's capability to select appropriate formulations depending on the route of administration by which the diagnostic compositions are administered to a human or animal being.

Thus, the diagnostic compositions in accordance with the present invention may be formulated for intravenous application, intramuscular application, oral application, nasal application, buccal application, sublingual application, and/or rectal application.

A person skilled in the art will also be capable of selecting appropriate amounts of the SPECT tracers to be used in the diagnostic compositions in accordance with the invention.

Typically, SPECT tracers that are capable of crossing the blood brain barrier and can associate with the Dopamine Transporter such as those mentioned in Table 1 will be applied in amounts as they are known to be pharmaceutically acceptable.

In the case of Altropane, a typical injected dose will be 185-300 MBq, typically corresponding to 10-15 ng of Altropane, depending on specific activity at time of injection.

For Datscan the injected dose will be 111-185 MBq.

In a preferred embodiment, the diagnostic composition for the differential diagnosis of Alzheimer's disease, Lewy-Body Dementia, and/or Frontotemporal Dementia will comprise Altropane together with pharmaceutically acceptable excipients.

The present invention not only considers the aforementioned diagnostic compositions, but also the use of at least one compound which is suitable for SPECT, capable of crossing the blood brain barrier, and can associate with a Dopamine Transporter in the manufacture of a diagnostic composition for the differential diagnosis of Alzheimer's disease, Lewy-Body Dementia, and/or Frontotemporal Dementia. As mentioned above, these tracer molecules may be typically labeled with $^{99m}$Tc and/or $^{123}$I. Reference is made to above and the structural elements which may be present in such tracer molecules and the other preferred embodiments of tracer molecules that may be used in the manufacture of diagnostic compositions.

If the diagnostic compositions in accordance with the invention are administered to a human or animal being, one can take SPECT images shortly after administration of the tracer in order to measure the perfusion, i.e. the initial distribution of the tracer within the brain. If one performs these measurements and compares the resulting images to those obtained from suitable control, one can differentiate Alzheimer's disease versus Frontotemporal Dementia.

The differential diagnosis between these two types of diseases becomes obvious from a decreased perfusion in the patient in distinct brain areas. In a patient suffering from Alzheimer's disease, a decreased perfusion in comparison to the control will be observed in e.g. in the tempoparietal cortex (sieheKoeppe et al. (2005), The Journal of Nuclear Medicine, 46: 936-944). Matsuda et al., vide supra).

If the patient suffers from Frontotemporal Dementia, a decreased perfusion will be seen mainly in the area of the frontal cortex (Koeppe et al, vide supra).

One will then continue to take SPECT images until a point in time when the SPECT tracers have associated with the Dopamine Transporters. This may be detected by recording e.g. the nigrostriatum. If one compares those images with images taken from a suitable control subject, it is possible to determine e.g. the functional integrity of the nigrostriatum and, by correlating these images with the images taken for determining perfusion shortly after administration, it is possible to also differentially diagnose Lewy-Body Dementia versus Frontotemporal Dementia.

For the purposes of the present invention, the term "suitable control" refers to a human or animal being which does not suffer from any form of dementia, particularly Alzheimer's disease, Lewy-Body Dementia, or Frontotemporal Dementia. A suitable control subject may also comprise a human or animal being that suffers from a specific type of dementia, i.e. Alzheimer's disease, Lewy-Body Dementia, or Frontotemporal Dementia, for which this specific disease has been confirmed.

The present invention in one embodiment, therefore, relates to a method of diagnosis comprising at least the following steps:
  administering at least one compound which is suitable for SPECT, which is capable of crossing the blood brain barrier and which can associate with a Dopamine Transporter (DAT) to a human or animal being;
  measuring said compound's distribution within the brain using SPECT at least at a time point $x_1$; and
  measuring said compound's association with DAT within the brain at least at a time point $x_2$, wherein $x_2$ is later than $x_1$;
  comparing the obtained results with an appropriate control;
  deciding on the occurrence of Alzheimer's disease, Lewy-Body
  Dementia and/or Frontotemporal Dementia.

In another embodiment, the present invention relates to a method of data acquisition comprising at least the following steps:
  administering at least one compound which is suitable for SPECT, which is capable of crossing the blood brain barrier and which can associate with a Dopamine Transporter (DAT) to a human or animal being;
  measuring said compound's distribution within the brain using SPECT at least at a time point $x_1$; and
  measuring said compound's association with DAT within the brain at least at a time point $x_2$, wherein $x_2$ is later than $x_1$.

The images obtained with this method of data acquisition may, of course, be used for comparison with a suitable control subject to then decide on the occurrence of Alzheimer's disease, Lewy-Body Dementia, and/or Frontotemporal Dementia.

A person skilled in the art will understand that the above-described are characterized in that, firstly, the perfusion, i.e. distribution, of the SPECT tracer is determined at a time point $x_1$ and that subsequently association with Dopamine Transporters is recorded at a time point $x_2$, wherein $x_2$ is later than x1.

Of course, a person skilled in the art is aware that SPECT images may be taken not only at one defined time point $x_1$ and a second time point $x_2$, but over a period of time, and that images of different time periods may be combined to determine the initial perfusion, i.e. distribution, and the later association with Dopamine Transporters.

A person skilled in the art will also clearly be aware that the above-described characteristics of the compounds to be used for diagnostic compositions in accordance with the invention equally apply if such compounds are to be used in the method of diagnosis and/or method of data acquisition.

Furthermore, a person skilled in the art is aware that the time period in which SPECT images are recorded and thus the time points which perfusion of the SPECT tracer and association of the SPECT tracer with a Dopamine Transporter will be determined may differ depending on the respective SPECT tracer.

A typical time period for imaging perfusion and thus distribution of the SPECT tracer will be in the range from 1 to 10 minutes, and preferably between 2 to 5 minutes.

This time period should be suitable for most SPECT tracers as described above to measure the initial distribution within the brain and thus to allow identification by correlating perfusion and metabolic activity in those brain areas which are affected by Alzheimer's disease and Frontotemporal Dementia.

As regards the second time point $x_2$, which is indicative of the time period by which the SPECT tracer will have associated with Dopamine Transporters, this time period will depend mainly on the characteristics of the respective tracer for localizing to the respective brain areas.

A person skilled in the art will be aware that this period and the time points may significantly vary for the different compounds. For example, if Datscan is used as a SPECT tracer in the diagnostic compositions and methods in accordance with the invention, an association with Dopamine Transporters, will typically be observed after three to four hours. If, however, Altropane is used as a SPECT tracer, association with Dopamine Transporters will typically be observed within 20 to 40 minutes and preferably around approximately 30 minutes.

In general, it may be preferred to use SPECT tracers which associate after a rather short time period with the Dopamine Transporter in order for the session to be as short as possible for the patient. Of course, a balance has to be found between the preferences of the patient and the properties of the SPECT tracer for differential diagnosis of the aforementioned types of dementia.

In a preferred embodiment, the diagnostic compositions, the SPECT tracer Altropane, and the above-described methods of data acquisition and diagnosis are undertaken using this tracer. In a typical embodiment, the time point $x_1$ will be in the range from about 1 to about 10 minutes and determination of association with the Dopamine Transporters will be in the range from about 15 to about 30 minutes.

In one aspect of the invention, from a dynamic image acquisition of more than 10 minutes, perfusion could be assessed using pharmacokinetic modeling.

Thus, the present invention in one embodiment relates to relates a method of diagnosis comprising at least the following steps:
administering at least one compound which is suitable for SPECT, which is capable of crossing the blood brain barrier and which can associate with a Dopamine Transporter (DAT) to a human or animal being;
measuring said compound's distribution within the brain at multiple time points;
assessment of brain perfusion by pharmacokinetic modeling;
measuring said compound's association with DAT within the brain at least at one later point in time;
comparing the obtained results with an appropriate control; and
deciding on the occurrence of Alzheimer's disease, Lewy-Body Dementia and/or Frontotemporal Dementia.

In another embodiment, the present invention relates to a method of data acquisition comprising at least the following steps:
administering at least one compound which is suitable for SPECT, which is capable of crossing the blood brain barrier and which can associate with a Dopamine Transporter (DAT) to a human or animal being;
measuring said compound's distribution within the brain at multiple time points;
assessment of brain perfusion by pharmacokinetic modeling; and
measuring said compound's association with DAT within the brain at least at one later point in time.

Again, the data obtained in such a method of data acquisition could be used for differentially diagnosing the above-mentioned various types of dementia.

In yet another aspect of the invention, both perfusion and association with DAT may be assessed by pharmacokinetic modeling. This aspect may preferably be performed with Altropane of table 1.

The present in one embodiment thus relates to also to method of diagnosis comprising at least the following steps:
administering at least one compound which is suitable for SPECT, which is capable of crossing the blood brain barrier and which can associate with a Dopamine Transporter (DAT) to a human or animal being, preferably being Altropane of table 1;
measuring said compound's distribution within the brain over a period of time being preferably approximately 0 to 45 min after administration;
measuring said compound's association with DAT within the brain at least at one later point in time;
assessment of brain perfusion and DAT association by pharmacokinetic modeling;
comparing the obtained results with an appropriate control; and
deciding on the occurrence of Alzheimer's disease, Lewy-Body Dementia and/or Frontotemporal Dementia.

Yet another embodiment relates to a method of data acquisition comprising at least the following steps:
administering at least one compound which is suitable for SPECT, which is capable of crossing the blood brain barrier and which can associate with a Dopamine Transporter (DAT) to a human or animal being, preferably being Altropane of table 1;
measuring said compound's distribution within the brain period of time being preferably approximately 0 to 45 min after administration;
measuring said compound's association with DAT within the brain at least at one later point in time; and
assessment of brain perfusion and DAT association by pharmacokinetic modeling.

Again, the data obtained in such a method of data acquisition could be used for differentially diagnosing the above-mentioned various types of dementia.

The SPECT technology as such is known to a person skilled in the art and well established in research facilities as well as hospitals. A person skilled in the art will, therefore, know how to select the appropriate equipment and how to set the appropriate parameters for taking reliable images of sufficient quality for a specific SPECT tracer.

The present invention provides for numerous advantages. One important advantages are that it is now possible to differentially diagnose the three degenerative forms of dementia Alzheimer's disease, Lewy-Body Dementia, and a Frontotemporal Dementia in a single SPECT session, which is not only a lot more comfortable for a patient than having to participate in a PET and a SPECT session, but, of course, is also preferable in terms of time and cost.

The invention will now be illustrated with respect to some of its preferred embodiments by describing specific examples. However, these examples are not to be construed as limiting the scope of the invention in any way.

Hypothetical Experiment

In the following, a hypothetical experiment is described that sets out the above-described diagnostic compositions and their use. A patient that is suspected of suffering from Alzheimer's disease, Lewy-Body Dementia, or Frontotemporal Dementia is analyzed in a SPECT session.

To this end, Altropane is administered to the patient at an amount of about 185-300 MBq.

Then, SPECT images are continuously recorded during a time period of 1 minute after administration of the tracer to approximately 45 minutes after administration.

Subsequently, images taken within the first five minutes that are most indicative of the perfusion of the tracers are compared with a control to assess for the presence of Alzheimer's disease or Frontotemporal Dementia. In a second step, images recorded in the time period of 20 to 30 minutes are selected and compared with a suitable control to assess for the functional integrity of the nigrostriatum.

Typical areas of hypo-perfusion (hypo-metabolism) indicative of Alzheimer's Disease are the temporoparietal cortex, posterior cingulated, and precuneus with relative sparing of sensorimotor cortex primary visual cortex, striatum and cerebellum.

Indicative of FTD is hypo-perfusion (hypo-metabolism) in frontal cortical areas (orbitomedial and dorsoloateral) with relative sparing of cingulated gyms. As in AD, the lateral temporal cortex might also show reduced activity.

Looking at integrity of dopamine transporters (DAT), reduced uptake, in particular in the putamen relative to caudate and/or left/right asymmetry is indicative of Dementia with Lewy-Bodies.

The invention claimed is:

1. A method of data acquisition for diagnosing and differentiating between different types of dementia, said method comprising:

administering at least one compound which is suitable for SPECT, which crosses a blood brain barrier and which is associated with a Dopamine Transporter (DAT) to a human or animal being, said at least one compound selected from the group consisting of Technepine, Fluoratec, TRECTEC-1, TRODAT-1, Altropane®, Dopascan, and DaTSCAN;

measuring a distribution associated with the at least one compound within the brain using SPECT at least at a time point x1;

measuring an association of the at least one compound with DAT within the brain at least at a time point x2 using SPECT, wherein x2 is later than x1; and diagnosing the different types of dementia selected from differentiating between Alzheimer's disease and Frontotemporal Dementia and between Lewy-Body Dementia and Frontotemporal Dementia based on measuring the distribution associated with the at least one compound to at least one particular portion of the brain and comparing images obtained using SPECT to images obtained using SPECT of a suitable subject, wherein the suitable subject is one of a human or animal being which does not suffer from any form of dementia, and wherein:

Alzheimer's disease is present when a decreased distribution in comparison to the suitable subject is noted;

Frontotemporal Dementia is present when a decreased distribution is present mainly in the area of the frontal cortex; and Lewy-Body Dementia is differentially diagnosed over Frontotemporal Dementia by correlating SPECT images with perfusion images obtained during administration of the at least one compound.

2. The method as recited in claim 1, wherein said at least one compound is labeled with at least one of $^{99m}$Tc and $^{123}$I.

3. The method as recited in claim 1, wherein said at least one compound is Technepine.

4. The method as recited in claim 1, wherein said at least one compound is Altropane®;

wherein the distribution within the brain of Altropane® is measured approximately 2 to 5 min after administration; and wherein the association of Altropane® with DAT within the brain is measured approximately 15 to 45 min after administration.

* * * * *